United States Patent [19]

Stephen et al.

[11] 4,077,941

[45] Mar. 7, 1978

[54] METAL SALTS OF N,N-DISUBSTITUTED β-ALANINES AND STABILIZED COMPOSITIONS

[75] Inventors: John F. Stephen, New City; John D. Spivack, Spring Valley, both of N.Y.

[73] Assignee: Ciba-Geigy Corporation, Ardsley, N.Y.

[21] Appl. No.: 679,255

[22] Filed: Apr. 21, 1976

Related U.S. Application Data

[63] Continuation of Ser. No. 449,881, Mar. 11, 1974, abandoned.

[51] Int. Cl.² ............................................. C08K 5/09
[52] U.S. Cl. .................... 260/45.75 N; 260/45.75 W; 260/45.75 H; 260/45.75 T; 260/45.75 G; 260/45.75 F; 260/45.85 A; 260/429 R; 260/429.5; 260/429.7; 260/429.9; 260/438.5 R; 260/439 R; 260/448 R; 260/534 C
[58] Field of Search ............ 260/439 R, 438.5, 429 R, 260/429.9, 448 R, 429.7, 429.5, 45.75 N, 45.75 H, 45.75 G, 45.75 T, 45.75 F, 45.85 A, 534 C, 45.75 W

[56] References Cited

U.S. PATENT DOCUMENTS

| | | | |
|---|---|---|---|
| 2,526,556 | 10/1950 | Gresham et al. | 260/534 C |
| 2,840,603 | 6/1958 | Mock et al. | 260/439 X |
| 2,883,406 | 4/1959 | Jeze | 260/429.9 |
| 3,008,814 | 11/1961 | Robbins | 44/63 |
| 3,037,997 | 6/1962 | Hewitt | 260/435 R |
| 3,054,750 | 9/1962 | Jolly | 44/71 |
| 3,102,107 | 8/1963 | Soeder | 260/45.75 N |
| 3,446,827 | 5/1969 | Schwartz et al. | 260/429.7 |
| 3,780,095 | 12/1973 | Klemm | 260/448 R |

FOREIGN PATENT DOCUMENTS

| | | |
|---|---|---|
| 70-1360 | 1/1970 | Japan. |
| 67-3183 | 2/1967 | Japan. |
| 67-3179 | 2/1967 | Japan. |
| 67-4275 | 2/1967 | Japan. |
| 918,365 | 2/1963 | United Kingdom. |

OTHER PUBLICATIONS

Chemical Abstracts, v74, 1274365d (1971).
Chemical Abstracts, v68, 14031(b) (1968).
Chemical Abstracts, v66, 11015u (1967).
Chemical Abstracts, v74, 23597s (1971).

*Primary Examiner*—Helen M. S. Sneed
*Attorney, Agent, or Firm*—Nestor W. Shust

[57] ABSTRACT

Compounds having the formula

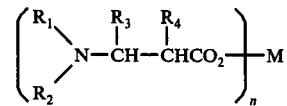

wherein
$R_1$ and $R_2$ are alkyl, cycloalkyl, phenyl, alkyl substituted phenyl, benzyl or alkyl substituted benzyl,
$R_3$ and $R_4$ are both independently hydrogen or lower alkyl,
M is a metal, and
n is a value of from 1 to 4, are good light stabilizers. The metal salts of this invention are prepared by reacting the appropriate amino acid or its alkali metal salt with a reactive form of the metal or metal complex.

19 Claims, No Drawings

METAL SALTS OF N,N-DISUBSTITUTED β-ALANINES AND STABILIZED COMPOSITIONS

This is a continuation of application Ser. No. 449,881 filed on Mar. 11, 1974, now abandoned.

BACKGROUND OF THE INVENTION

This invention relates to the stabilization of organic material normally tending to deteriorate. In particular, the invention relates to the protection of synthetic polymers against the harmful degradative effects, such as discoloration and embrittlement caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate spot and degrade. The rate of air oxidation of polyolefins such as polyethylene and polypropylene is materially accelerated by ultraviolet light.

It is also known to use certain metal salts of aminoacids for the stabilization of polyolefins against degradation by heat and light and as dyesites. For example, in U.S. Pat. No. 3,102,107, nickel salts of α-aminocarboxylic acids are disclosed as stabilizers of polyolefins against degradation by light. In Japanese Pat. Nos. 4275/67, 3183/67, and 3179/67, there are disclosed certain metal salts of N-alkyl-β-aminopropionates as additives for dyeable polyolefin compositions. We have now found that if, instead of the above metal salts of amino acids, certain metal salts of N,N-disubstituted β-alanines are used as stabilizers for organic materials against degradation by light, a significant and unexpected enhancement in light stabilizing activity results.

DETAILED DISCLOSURE

The present invention is accordingly directed to a new class of ultraviolet light stabilizers which consist of a compound of the formula

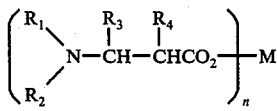

wherein $R_1$ and $R_2$ independently of each other are alkyl, phenyl, phenyl substituted with 1 or 2 alkyl groups, cycloalkyl having 5 to 6 carbon atoms, benzyl, or benzyl substituted with an alkyl group on the phenyl nucleus;

$R_3$ and $R_4$ are both independently hydrogen and lower alkyl,

M is a member selected from the group consisting of nickel, iron, chromium, manganese, zinc, aluminum, tin, dialkyl tin and titanium; and $n$ has a value of from 1 to 4, the value of $n$ being the same as the available valence of M.

Copper and cobalt are additional members which may be represented by M above.

In a preferred embodiment of the compound of formula I, $R_1$ and $R_2$ independently of each other are alkyl having from 1 to 18 carbon atoms, cyclohexyl, phenyl, phenyl having an alkyl group of 1 to 12 carbon atoms at the 4-position of the phenyl ring, benzyl or benzyl having an alkyl group of 1 to 12 carbon atoms at the 4-position of the phenyl ring;

$R_3$ and $R_4$ are independently hydrogen and methyl,

M is a member selected from the group consisting of nickel, chromium, manganese, zinc, aluminum, tin and dialkyl tin, where the alkyl group is from 4 to 8 carbon atoms, and $n$ has a value of from 1 to 4, the value of $n$ being the same as the available valence of M.

In a more preferred embodiment of the compound of formula I, $R_1$ is alkyl having 1 to 18 carbon atoms, especially lower alkyl, and $R_2$ is alkyl having 1 to 18 carbon atoms, phenyl, phenyl having an alkyl group of 1 to 12 carbon atoms at the 4-position of the phenyl ring, cyclohexyl, benzyl, or benzyl having an alkyl group of 1 to 12 carbon atoms at the 4-position of the phenyl ring; or $R_1$ and $R_2$ are each alkyl having 1 to 18 carbon atoms;

$R_3$ and $R_4$ are both independently hydrogen and methyl;

M is a member selected from the group consisting of nickel, chromium, manganese, zinc, aluminum, tin and dibutyltin; and $n$ has a value of from 1 to 4, the value of $n$ being the same as the available valence of M.

In the most preferred embodiment of the compounds of formula I, $R_1$ and $R_2$ are independently of each other alkyl of from 1 to 18 carbon atoms, M is a member selected from the group consisting of nickel, manganese, zinc and chromium, and $R_3$, $R_4$ and $n$ are as defined previously.

The stabilizers of this invention are useful in protecting various organic materials against degradation by actinic light. It is understood that some compounds within the scope of this invention are more useful for the stabilization of particular organic materials while others are more useful for other organic substrates. It has been found that within the general concept of this invention compounds of formula I, where $R_1$ is lower alkyl, preferably methyl, $R_2$ is alkyl having from 4 to 18 carbon atoms, $R_3$ and $R_4$ are hydrogen, and the other symbols are as defined in formula I above, are particularly useful in stabilizing polyolefins, for example polypropylene.

This invention also relates to compositions of matter which are stabilized against ultraviolet light deterioration which comprises a synthetic organic polymer normally subject to ultraviolet deterioration containing from about 0.005% to 5% by weight of the polymer of the compounds of formula I and preferably from 0.01% to 2% by weight.

The compounds of this invention are stabilizers of organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, α,β-unsaturated acids, α, β-unsaturated esters, α,β-unsaturated ketones, α,β-unsaturated aldehydes and unsaturated hydrocarbons such as butadienes and styrene; poly-α-olefins such as high and low density polyethylene, cross-linked polyethylene, chlorinated polyethylene, polypropylene, poly(4-methylpentene-1) and the like, including copolymers of α-olefins; such as ethylene-propylene copolymers, and the like; terpolymers of ethylene-propylene with a diene, e.g., hexadiene, dicylopentadiene, ethylidenenorbornene; dienes such as polybutadiene, polyisoprene, and the like, including copolymers with other monomers; polyurethanes such as are prepared from polyols and organic polyisocyanates, and polyamides such as polyhexamethylene adipamide and polycaprolactam; polyesters such as polyethylene terephthalates; polycarbonates such as those prepared from bisphenol-A and phosgene; polyacetals such as polyethylene terephthalate polyacetal; polystyrene, polyethyleneoxide; polyacrylics such as polyacrylonitrile; polyphenylenoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene)-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethyleneglycol, methoxytriethyleneglycol, triethylene glycol, octaethyleneglycol, dibutyleneglycol, dipropyleneglycol and the like.

The compounds of this invention are particularly useful as UV light stabilizers, especially for the protection of polyolefins, for instance, polyethylene, polypropylene, poly(butene-1), poly(pentene-1), poly(3-methylbutene-1), poly(4-methylpentene-1), various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur-containing esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and the other chemicals used in rubber compounding, plasticizers, color stabilizers, di- and tri-alkyl- and -alkylphenylphosphites, heat stabilizers, ultraviolet light stabilizers, ultraviolet absorbers, such as benzotriazoles and benzophenones, benzoates and other metal salts, antiozonants, dyes, pigments, buffers, such as calcium stearate, magnesium stearate, zinc stearate, metal chelating agents, dyesites such as organometallic derivatives, e.g., nickel acetate, octoate and stearate, organic basic dyesites, e.g., polyalkylene pyridine derivatives, and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

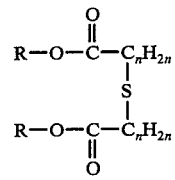

wherein R is an alkyl group having from 6 to 24 carbon atoms; and $n$ is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer, namely, from about 0.005% to 5% and preferably from 0.01% to 2% by weight. Representative of such antioxidants are phosphite esters, such as triphenylphosphite and dibutylphosphite and alkyl arylphosphites such as dibutylphenylphosphite, and the like.

The best results have been obtained with the preferred class of stabilizers, the hindered phenols. These compounds have been found to provide the best thermal stabilization with the least discoloration in the compositions of the invention. Among these phenolic stabilizers are included the following:
di-n-octadecyl(3-butyl-4-hydroxy-5-methylbenzyl)malonate
2,6-di-t-butylphenol
2,2'-methylene-bis(6-t-butyl-4-methylphenol)
2,6-di-t-butylhydroquinone
octadecyl-(3,5-di-t-butyl-4-hydroxybenzylthio)acetate
1,1,3-tris(3-t-butyl-6-methyl-4-hydroxyphenyl)butane 1,4-bis(3,5-di-t-butyl-4-hydroxybenzyl)-2,3-5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl-β-(3,5-di-t-butyl-4-hydroxyphenyl) propionate
n-octadecyl-3,5-di-t-butyl-4-hydroxybenzoate
2-(n-octylthio)ethyl-3,5-di-t-butyl-4-hydroxybenzoate
stearamido N,N-bis-{ethylene 3-(3,5-di-t-butyl-4-hydroxyphenyl)propionate}
1,2-propylene glycol bis-{3-(3,5di-t-butyl-4-hydroxyphenyl)propionate}
pentaerythritol tetrakis-{3-(3,5-di-t-butyl-4-hydroxyphenyl)propionate}
dioctadecyl-3,5-di-t-butyl-4-hydroxybenzylphosphonate
di-n-octadecyl-1-(3,5-di-t-butyl-4-hydroxyphenyl)-ethanephosphonate.

The above phenolic hydrocarbon stabilizers are known and many are commercially available.

The above antioxidants have been listed only for the purpose of illustration and it is important to note that any other antioxidant can be employed with similar improved results. The above exemplified antioxidants and other related antioxidants which are incorporated herein by reference, are disclosed in greater detail in the following patents: Netherlands patent specification No. 67/1119, issued Feb. 19, 1968; Netherlands patent specification No. 68/03498 issued Sept. 18, 1968; U.S. Pat. Nos. 3,255,191; 3,330,859, 3,644,482, 3,281,505; 3,531,483, 3,285,855; 3,364,250; 3,368,997; 3,357,944 and 3,758,549.

The compounds of this invention are also useful as dyesites for polyolefin materials, such as fibers and filaments.

The compounds of Formula I can be made by methods known in the art. For example, they may be prepared by reacting an amine of the formula

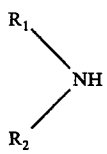   II wherein $R_1$ and $R_2$ are as previously defined with a compound of the formula

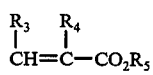   III wherein $R_3$ and $R_4$ are as defined previously, and $R_5$ is lower alkyl, preferably methyl or ethyl, followed by hydrolysis of the ester with a strong base, as e.g., an alkali metal hydroxide, acidification with a mineral acid, and finally treatment of the resulting acid or an alkali metal salt thereof with a reactive form of the metal. Thus, for example, a sodium or potassium salt of the present invention is treated with nickel chloride. In a similar fashion use of other halides such as manganese dichloride, aluminum chloride, and the like results in formation of the corresponding metal derivative.

The products of the addition of various secondary amines to acrylate esters are described, e.g., in U.S. Pat. No. 2,835,582; A. L. Mndzuhoyan et al, Arm. Khem. Zh, 23 (4), 258 (1970); D. W. Adamson, J. Chem. Soc., 1949 Supp. Issue No. 1 S144-55; D. Edwards et al, J. Pharm. Pharmacol, 16(9), 618(1964); C. Weisel et al, J. Am. Chem. Soc. 67, 1071(1945). Acid counterparts of the compounds of Formula I are described in T. L. Gresham et al, J. Am. Chem. Soc., 73, 3168 (1951); V. M. Solov'er et al, Zhur, Obschei Khim., 31, 2577 (1961); A. N. Kost, C. A. 47, 9906 f; and A. N. Kost, J. Gen. Chem. (U.S.S.R.) 16, 859(1946).

In a variation of the above procedure, acrylonitrile or a methacrylonitrile may be used in place of the compound of formula III with subsequent hydrolysis of the intermediate N,N-disubstituted β-aminopropionitrile to the corresponding acid. Thereafter, conversion to the acid salt proceeds as outlined above.

Compounds of the invention of the formula

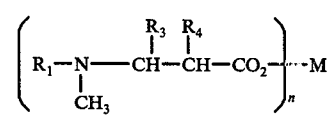   IV may be prepared by reacting an amine of the formula

   V wherein $R_1$ is as previously defined with a compound of the formula

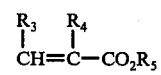   III wherein $R_3$, $R_4$ and $R_5$ are as defined previously. Subsequent N-methylation, and hydrolysis of the ester, acidification with a mineral acid, and treatment of the resulting acid with a reactive form of the metal, as mentioned above, yield the compound of formula IV.

In a variation of the immediately preceding procedure, acrylonitrile or a methacrylonitrile may be used in place of the compound of formula III.

The products of the addition of various secondary amines to acrylonitrile are described in J. H. Burckhalter et al., J. Am. Chem. Soc., 65, 2012 (1943).

An alternate method of preparing stabilizers of this invention involves reacting a lower alkyl β-halopropionate ester or nitrile with a secondary amine to yield the β-di-hydrocarbylamino-propionate ester or nitrile which is then hydrolyzed to the corresponding carboxylic acid or alkali metal salt and converted to the metal salt as described above.

The starting amines and unsaturated esters and nitriles used in the preparation of the compounds of this invention are either known materials or are preparable via known methods from known materials.

Among the amines useful in the present invention are included the following:
dicyclohexylamine
dicyclopentylamine
benzylmethylamine
benzylamine
aniline p-toluidine
m-toluidine
diphenylamine
methylethylamine
cycohexylamine
n-pentylamine
p-dodecylbenzylamine
2,4-dimethylaniline
diisobutylamine
diisopropylamine
dimethylamine
3,4-dimethylaniline
2,5-dimethylaniline
2,4-dimethylbenzylamine
2,5-dimethylbenzylamine
1,2-dimethylbutylamine
1,5dimethylhexylamine
di-n-tetradecylamine
dodecylamine
octadecylamine
tert-octylamine
n-octylamine
n-pentadecylamine
N-phenylbenzylamine
tetradecylamine
aminopentane
tert-butylamine
sec-butylamine
propylamine
n-tridecylamine
p-n-butylaniline.

Included among the compounds of this invention are the following:
nickel bis(N-methyl-N-isoamyl-$\beta$-alanine)
manganese bis($\alpha,\beta$-dimethyl-di-n-propyl-$\beta$-alanine)
cobalt bis(N-methyl-N-p-tert-octylphenyl-$\beta$-alanine)
nickel bis(N-p-n-dodecylbenzyl-N-n-hexyl-$\beta$-alanine)
di-n-butyltin bis(N-methyl-N-n-octadecyl-$\beta$-alanine)
nickel bis($\alpha$-methyl-$\beta$-n-propyl-di-N-n-octyl-$\beta$-alanine)
nickel bis(N,N-dicyclohexyl-$\beta$-alanine)
nickel bis(N,N-diphenyl-$\beta$-alanine)
nickel bis(N,N-dibenzyl-$\beta$-alanine) nickel bis(N-methyl-N-benzyl-$\beta$-alanine) nickel bis(N-methyl-N-cyclohexyl-$\beta$-alanine).

The following examples, presented for illustration and not limitation, will further serve to typify the nature of the present invention.

EXAMPLE 1

Ethyl $\beta$-(N-methyl-n-butylamino)-propionate

A. A stirred mixture of N-methyl-n-butylamine (42.8 g., 0.49 mole) and ethyl acrylate (55 g., 0.54 mole) was heated at 80°–90° C for 20 hours. Excess acrylate was evaporated under reduced pressure, and the residue distilled to give 80.0 g (87%) of the title compound, b.p. 97° C at 12 mm.

B. By essentially following the above procedure (A) and substituting for the N-methyl-n-butylamine an equivalent amount of
(a) N-methyl-n-octadecylamine
(b) N-methyl-n-octylamine
(c) di-n-propylamine
(d) diethylamine
there are respectively obtained:
(a) ethyl $\beta$-(N-methyl-n-octadecylamino)-propionate
(b) ethyl $\beta$-(N-methyl-n-octylamino)-propionate
(c) ethyl $\beta$-(di-n-propylamino)-propionate
(d) ethyl $\beta$-diethylamino)-propionate.

C. By essentially following the above procedure (A) and substituting an equivalent amount of N-methyl-n-octadecylamine for the N-methyl-n-butylamine and an equivalent amount of ethyl crotonate and methyl methacrylate for the ethyl acrylate there were respectively obtained
(a) ethyl $\beta$-(N-methyl-n-octadecylamino)-$\beta$-methyl propionate
(b) methyl $\beta$-(N-methyl-n-octadecylamino)-$\alpha$-methyl propionate.

D. By essentially following the above procedure (A) and substituting an equivalent amount of acrylonitrile for the ethyl acrylate and an equivalent amount of di-n-octylamine for the N-methyl-n-butylamine there was obtained $\beta$-(di-n-octylamino)-propionitrile.

EXAMPLE 2

Ethyl-$\beta$-(p-n-butylphenylamino)-propionate

A. A mixture of freshly distilled p-n-butylaniline (44.6 g., 0.3 mole) and 5 ml of acetic acid was heated at 80° for 10 minutes. Ethyl acrylate (33 g., 0.33 mole) was added over a 30 minute period with the temperature at 80°–85° C. After the addition was completed the mixture was heated at 80°–85° C for 20 hours. The cold mixture was dissolved in ether and the other solution washed with aqueous sodium bicarbonate and water. The dried ($Na_2So_4$) ether solution was evaporated to give 74.2 g of crude ester. Distillation gave 53.7 g (72%) of the title compound as the friction with b.p. 122°–125° at 0.01 mm.

B. By essentially following the above procedure (A) and substituting for the p-n-butylaniline an equivalent amount of p-n-dodecylaniline, there was obtained ethyl-$\beta$-(p-n-dodecylphenylamino)-propionate.

EXAMPLE 3

Ethyl $\beta$-(N-methyl-p-n-butylphenylamino)-propionate

A. To a stirred solution of ethyl $\beta$-(p-n-butylphenylamine)-propionate (37.4 g., 0.15 mole) in 22 ml of methanol was added a solution of 0.75 g. of sodium chloride in 11.5 ml of water. The mixture was warmed to 50° C and 15 ml of 90% formic acid solution was added dropwise, the temperature rising to 62° C. Ten minutes after the addition of formic acid was completed, 13.5 ml of 37% aqueous formaldehyde was added at such a rate that the vigorous evolution of carbon dioxide was kept under control. After the addition was completed the mixture was heated at 55°–60° for approximately 18 hours. The pH of the cold mixture was adjusted to 7 by adding aqueous sodium hydroxide and the organic phase was extracted with ether. After washing with water, the dried ($Na_2S0_4$) solution was evaporated in vacuo to give 39.2 g (99%) of crude ester as a light yellow oil.

B. By essentially following the above procedure (A) and substituting for the ethyl-$\beta$-(p-n-butylphenylamino)-propionate an equivalent amount of
(a) ethyl $\beta$-(N-p-n-dodecylphenylamino)propionate
(b) $\beta$-(n-dodecylamino)-propionitrile there is respectively obtained
(a) ethyl-$\beta$-(N-methyl-p-n-dodecylphenylamino)-propionate
(b) $\beta$-(N-methyl-n-dodecylamino)-propionitrile.

EXAMPLE 4

N-methyl-N-n-butyl-β-alanine hydriochloride

A. A stirred solution of ethyl-β-(N-methyl-n-butylamino)-propionate (49 g, 0.423 mole) in 250 ml of ethanol was treated with aqueous sodium hydroxide (20 g., 0.5 mole in 50 ml of water) The mixture was refluxed for 20 hours. The pH of the cold mixture was adjusted to pH 6.3 (pH meter) by the addition of dilute hydrochloric acid. The precipitated sodium chloride was collected by filtration, and filtrate was evaporated to dryness under reduced pressure. The oily residue thus obtained was dissolved in isopropanol, and the solution filtered to remove the sodium chloride. The filtrate was evaporated under reduced pressure and the resulting oily residue was heated at 70° C and 0.02 mm for 18 hours. The viscous residue of 63 g was then dissolved in 250 ml of acetone and the solution clarified by filtration. The filtrate was saturated with hydrogen chloride when 68.7 g (83%) of amino acid hydrochloride, m.p. 124°-127° C, crystallized from solution. Purity was established as 99.3% by titration with perchloric acid in acetic acid in the presence of mercuric acetate.

B. By essentially following the above procedure
1. The following esters were saponified to give the sodium salts of the corresponding amino acids which were isolated in perference to the corresponding hydrochlorides:
(a) ethyl β-(N-methyl-n-octadecylamino)-propionate
(b) ethyl β-(N-methyl-n-octadecylamino)-β-methyl propionate
(c) methyl β-(N-methyl-n-octadecylamino)-α-methyl propionate.

2. The following esters and nitrile were saponfied to give the corresponding free aminoacids which were isolated as such:
(a) ethyl β-(N-methyl-n-octylamino)-propionate
(b) ethyl β-(N-methyl-p-n-dodecylphenylamino)-propionate
(c) ethyl β-(N-methyl-p-n-butylphenylamino)-propionate
(d) ethyl β-(diethylamino)-propionate
(e) ethyl β-(di-n-propylamino)-propionate
(f) β-(di-n-octylamino)-propionitrile.

C. β-(N-methyl-n-dodecylamino)-propionitrile was saponified under essentially similar conditions to give the sodium salts of N-methyl-N-n-dodecyl-β-alanine.

EXAMPLE 5

Nickel bis(N-methyl-N-n-butyl-β-alanine)

To a stirred solution of the amino acid hydrochloride of Example 4 (9.78 g 0.05 mole) in 100 ml of methanol was added 100 ml of a solution in 1N potassium hydroxide in methanol. The mixture was heated to 50° C and a solution of nickel chloride hexahydrate (5.94 g., 0.025 mole) in 50 ml of methanol was added dropwise during 1 hour. During the addition the temperature was kept at 50° C for an additional hour. The precipitated potassium chloride was collected by filtration, and the filtrate was evaporated to dryness in vacuo. The green residue thus obtained was dissolved in heptane and the solution filtered from insoluble potassium chloride. The filtrate was evaporated under reduced pressure and the residue heated at 60°-70° and 0.05 mm. for approximately 6 hours. The green residue was then dissolved in heptane, the heptane solution filtered, the solvent evaporated under reduced pressure, and the residue heated at 70°-80° and 0.05 mm for 18 hours to give 9.1 g (97%) of the desired nickel salt as a viscous green oil.

Analysis for $C_{16}H_{32}N_2NiO_4$: Calculated: Ni, 15.65% Found: Ni, 15.48%

EXAMPLE 6

Nickel bis(N-methyl-N-p-n-butylphenyl-β-alanine)

A. To a stirred solution of N-methyl-p-n-butylphenyl-β-alanine (7.85 g., 0.03 mole) in 250 ml of water was added 15 ml. of 2N sodium hydroxide solution. The hazy solution was clarified by filtration, and a solution of nickel chloride hexahydrate (3.58 g., 0.015 mole) in 50 ml of water was added dropwise to the filtrate. The nickel salt precipitated from solution during the addition, and after the addition was completed the mixture was stirred at room temperature for three hours. The precipitated nickel salt was filtered off and washed with water. After drying for 72 hours over $P_2O_5$ the salt was dissolved in benzene. The benzene solution was filtered, the filtrate evaporated and the green residue thus obtained heated at 80°-85° at 0.01 mm for 17 hours to give 7 g (90%) of the title compound.

Analysis for $C_{28}H_{40}N_2NiO_4$: Calculated: Ni, 11.13% Found: Ni, 11.03%

B. By essentially following the above procedure (A) and substituting for the N-methyl-N-p-n-butylphenyl-β-alanine an equivalent amount of N,N-di-n-octyl-β-alanine there was obtained nickel bis(N,N-di-n-octyl-β-alanine).

Analysis for $C_{38}H_{76}N_2NiO_4$: Calculated: Ni, 8.58% Found: Ni, 8.62%

EXAMPLE 7

Nickel bis(N-methyl-N-n-octadecyl-β-alanine)

A. A stirred solution of the sodium salt of N-methyl-N-n-octadecyl-β-alanine (neutralization equivalent- 384), 7.6 g., 0.02 mole, in 150 ml of a methanol-isopropanol mixture (1:2) at 50° was treated dropwise during 15 minutes with a solution of nickel chloride hexahydrate, 2.38 g, 0.01 mole) in 45 ml of a methanol-isopropanol mixture (1:2). When the addition was completed the mixture was stirred and refluxed for 16 hours. The mixture was evaporated to dryness under reduced pressure and the resulting green oil was dissolved in benzene. After filtration to remove sodium chloride, the filtrate was evaporated in vacuo. The residual oil was dissolved in hexane and the hexane solution was filtered to remove a small amount of sodium chloride. Evaporation of the hexane under reduced pressure gave 7.05 g of the title compound as a waxy solid after heating at 60°-70°/4 mm.

Analysis for $C_{44}H_{88}N_2NiO_4$: Calculated: Ni, 7.65% Found: Ni, 7.30%

B. By essentially following the above procedure (A) and substituting for the sodium salt of N-methyl-N-n-octadecyl-β-alanine equivalent amounts of the sodium salts of
(a) N-methyl-N-n-dodecyl-β-alanine
(b) α-methyl-N-methyl-N-n-octadecyl-β-alanine
(c) β-methyl-N-methyl-N-n-octadecyl-β-alanine
there were respectively prepared:
(a) nickel bis(N-methyl-N-n-dodecyl-β-alanine)
Analysis for $C_{32}H_{64}N_2NiO_4$ Calculated: Ni, 9.79% Found: Ni, 9.79%
(b) nickel bis(α-methyl-N-methyl-N-n-octadecyl-β-alanine)

Analysis for $C_{46}H_{92}N_2NiO_4$ Calculated: Ni, 7.38%
Found: Ni, 7.19%

(c) nickel bis(β-methyl-N-methyl-N-n-octadecyl-β-alanine)

Analysis for $C_{46}H_{92}N_2NiO_4$ Calculated: Ni, 7.38%
Found: Ni, 7.14%

C. By essentially following the above procedure (A) and substituting the following metal complexes for nickel chloride
(a) zinc chloride
(b) manganese chloride
(c) chromium trichloride
(d) cobalt(ous) chloride
(e) copper chloride and using ethanol as a solvent there were respectively obtained (a) Zinc bis(N-methyl-N-n-octadecyl-β-alanine), m.p. 47°–49°
Analysis for $C_{44}H_{88}N_2O_4Zn$ Calculated: Zn, 8.42%
Found: Zn, 8.21%

(b) Manganese bis(N-methyl-N-n-octadecyl-β-alanine), m.p. 42°–44°
Analysis for $C_{44}H_{88}N_2O_4Mn$ Calculated: Mn, 7.15%
Found: Mn, 7.44%

(c) Chromium tris(N-methyl-N-n-octadecyl-β-alanine), m.p. 48°–50°
Analysis for $C_{66}H_{132}N_3O_6Cr$ Calculated: Cr, 4.66%
Found: Cr, 4.53%

(d) Cobalt bis(N-methyl-N-n-octadecyl-β-alanine)
(e) Copper bis(N-methyl-N-n-octadecyl-β-alanine).

EXAMPLE 8

Nickel bis(N,N-di-n-propyl-β-alanine)

A. A stirred suspension of N,N-di-n-propyl-β-alanine (98.5%; 17.55 g., 0.01 mole) in 50 ml of methanol was added 100 ml of a 1N KOH in methanol solution. The mixture was heated to 50° and then treated dropwise during 30 minutes with a solution of nickel chloride hexahydrate (98.4%; 12.05 g, 0.05 mole) in 60 ml of methanol. After the addition was completed, the mixture was heated at 50° for 2.5 hours. The methanol was evaporated under reduced pressure and the residue taken up in benzene. After removal of the potassium chloride by filtration the filtrate was evaporated to dryness in vacuo. The residue was dissolved in benzene-heptane mixture, filtered, evaporated and the residual glass was heated at 70°/0.01 mm for 17 hours to give 20.1 g of the desired nickel complex as a green glass.

Analysis for $C_{18}H_{36}N_2NiO_4$ Calculated: Ni, 14.55%
Found: Ni, 14.29%

B. By essentially following the above procedure (A) and substituting for the N,N-di-n-propyl-β-alanine an equivalent amount of
(a) N,N-diethyl-β-alanine
(b) N-methyl-N-p-n-dodecylphenyl-β-alanine
(c) N-methyl-N-n-octyl-β-alanine there were respectively prepared (a) Nickel bis(N,N-diethyl-β-alanine)
Analysis for $C_{14}H_{28}N_2NiO_4$ Calculated: Ni, 16.91%
Found: Ni, 16.69%

(b) Nickel bis(N-methyl-N-p-n-dodecylphenyl-β-alanine)
Analysis for $C_{44}H_{72}N_2NiO_4$ Calculated: Ni, 7.81%
Found: Ni, 7.63%

(c) Nickel bis(N-methyl-N-n-octyl-β-alanine)
Analysis for $C_{24}H_{48}N_2NiO_4$ Calculated: Ni, 12.04%
Found: Ni, 12.00%

EXAMPLE 9

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted on polymers using an artificial light exposure device is described below:

(a) Sample Preparation 5 mil Film — Unstabilized polypropylene powder (Hercules Profax 6501) is thoroughly blended with the indicated amounts of additives. The blended material is then milled on a two roll mill for 5 minutes at 182° C. The milled sheet is then compression molded at 220° C into 5 mil (.0127 cm) thick film under a pressure of 175 psi (12.30 kg/sq. cm) and water cooled in the press.

(b) Testing Method

This test is conducted in a FS/BL unit, basically of the American Cyanamid design, which consists of 40 tubes of alternating fluorescent sunlamps and black lights (20 of each). The 5 mil (.0127 cm) sample film which are mounted on 3 inches (7.62 cm) × 2 inches (5.08 cm) IR card holders with ¼ inch (0.635 cm) × 1 inch (2.54 cm) windows and are placed on a rotating drum 2 inches (5.08 cm) from the bulbs in the FS/BL unit. The time in hours is noted for the development 0.5 carbonyl absorbance units as determined on an Infrared Spectrophotometer. The development of carbonyl functional groups in the polymer is proportional to the amount of degradation caused by the ultraviolet light exposure.

The test results reported below were obtained according to the procedures described above. The amounts of the additives are expressed in weight percent based on the weight of the polymer.

TABLE I

| Additive | Time in Hours to 0.5 Carbonyl Absorbance Units | |
|---|---|---|
|  | Formulation A* | Formulation B** |
| Nickel bis(N-methyl-N-n-octyl-β-alanine) | 980 | 1210 |
| Nickel bis(N-methyl-N-n-dodecyl-β-alanine) | 990 | 1380 |
| Nickel bis(N-methyl-N-n-octadecyl-β-alanine) | 530 | 940 |
| Nickel bis(N-methyl-N-n-butyl-β-alanine) | 1080 | 1290 |
| Nickel bis(N-methyl-N-p-n-butylphenyl-β-alanine) | 380 | 680 |
| Nickel bis(N-methyl-N-p-n-dodecylphenyl-β-alanine) | 480 | 1010 |
| Nickel bis(N,N-di-n-propyl-β-alanine) | 1295 | 1430 |
| Nickel bis(N,N-diethyl-β-alanine) | 1300 | 1515 |
| Nickel bis(N,N-di-n-octyl-β-alanine) | 1110 | 1560 |
| Nickel bis(β-methyl-N-methyl-N-n-octadecyl-β-alanine) | 590 | 1155 |
| Nickel bis(α-methyl-N-methyl-N-n-octadecyl-β-alanine) | 645 | 930 |
| Zinc bis(N-methyl-N-n-octadecyl-β-alanine) |  | 830 |
| Chromium tris(N-methyl-N-n-octadecyl-β-alanine) |  | 920 |

TABLE I-continued

| | Time in Hours to 0.5 Carbonyl Absorbance Units | |
|---|---|---|
| Additive | Formulation A* | Formulation B** |
| Blank | 250 | 590 |

*Formulation A contains 0.5% additive and 0.2% antioxidant dioctadecyl 3,5-di-t-butyl-4-hydroxybenzylphosphonate.
**Formulation B contains 0.25% additive, 0.25% UV absorber 2(2'-hydroxy-3',5'-di-t-butylphenyl)-5-chlorobenzotriazole, and 0.2% antioxidant dioctadecyl 3,5-di-t-butyl-4-hydroxybenzylphosphonate.

Proportionately good stabilization is obtained when in the compositions of Table I the compounds of this invention are present in the concentrations of 0.1% and 1%.

Other hindered phenolic antioxidants may be used in place of di-octadecyl(3,5-di-t-butyl-4-hydroxybenzyl)-phosphonate in the above mentioned compositions for example, di-n-octadecyl α-(3-t-butyl-4-hydroxy-5-methylbenzyl)malonate, 2,4-bis (n-octylthio)-6-(3,4-di-butyl-4-hydroxyaniline)1,3,5-triazine, octadecyl 3-(3',5'-di-t-butyl-4'-hydroxyphenyl)propionate, pentaerythritol-tetrakis{3-(3,5-di-t-butyl-4-hydroxyphenyl)propionate}, tris-(3,5-di-t-butyl-4-hydroxybenzyl)isocyanurate, 2,6-di-tert-butyl-4-methylphenol, N,N,N-tris-(3,5-di-tert-butyl-4-hydroxybenzyl)isocyanurate, and 2,4,6-tris(3,5-di-tert-butyl-4-hydroxybenzyl)-1,3,5-trimethylbenzene.

The compositions of Table I are also stabilized when 2(2'-hydroxy-3',5'-di-t-butylphenyl)-5-chlorobenzotriazole is replaced with the following UV absorbers:

(a) 2-hydroxy-4-methoxy-5-sulfobenzophenone trihydrate
(b) 2-hydroxy-4-n-octoxybenzophenone
(c) {2,2'-thiobis(4-t-octylphenolate)}-n-butylamine nickel II
(d) p-octylphenyl salicylate
(e) 2,2'-dihydroxy-4,4'-dimethoxybenzophenone
(f) 2-(2'-hydroxy-5'-methylphenyl)-benzotriazole.

EXAMPLE 10

Outdoor Exposure Tests

Nickel bis(N-methyl-N-n-octadecyl-β-alanine) was solvent blended onto polypropylene powder (Hercules Profax 6501) in the indicated amounts, the powder was agitated for 5 minutes in a Kitchen Aid planetary mixer and the powder mixture was dried in a vacuun oven at a vacuum of 30 inches of water overnight.

The polypropylene powder containing the additives was extruder compounded at 232° C into pellets, and the pellets were melt spun at 260° C into 15 denier monofilaments using a 10 mil (0.0254 cm) orifice monofilament spinerett. The monofilaments were air cooled and oriented at a 4:1 ratio between hot (125° C) and gold godets and wound onto a fiber spool. The monofilament was mounted on wooden exposure frames and exposed at 45° south direct weathering inland in Florida. Samples were removed from exposure periodically and tensile tested on the Instron Table Model tensile tester under fiber grips.

The results indicated below show the percent retention of tensile strength after the indicated Kilolangleys of Florida Exposure. A Langley is a measure of energy in the ultraviolet region to which the samples have been exposed.

TABLE II

| | Florida Exposure | | | | | |
|---|---|---|---|---|---|---|
| | 15 Denier (nominal) monofilaments Percent Retention of Tensile Strength after Indicated Kilolangleys of Florida Exposure | | | | | |
| Formulation * | 30 | 45 | 60 | 70 | 80 | 90 |
| 0.25% nickel bis(N-methyl-N-n-octadecyl-β-alanine) | 80% | 62% | 31% | Brittle | | |
| 0.50% nickel bis(N-methyl-N-n-octadecyl-β-alanine) | 92% | 73% | 65% | 68% | 49% | 36% |
| 0.75% nickel bis(N-methyl-N-n-octadecyl-β-alanine | 91% | 81% | 66% | 69% | 52% | 57% |
| 0.25% nickel bis(N-methyl-N-n-octadecyl β-alanine) + 0.25% 2(2'-hydroxy-3',5'-di-t-butylphenyl)-5-chlorobenzotriazole | 92% | 84% | 61% | 56% | 33% | 27% |
| 0.25% {2,2'-thiobis(4-t-octylphenolato)}n-butylamine nickel (II) | 74% | 12% | Brittle | | | |
| 0.50% {2,2'-thiobis(4-t-octylphenolato)}n-butylamine nickel (II) | 80% | 23% | Brittle | | | |
| 0.75% {2,2'-thiobis(4-t-octylphenolato)}n-butylamine nickel (II) | 82% | 67% | 20% | Brittle | | |
| 0.25% {2,2'-thiobis(4-t-octylphenolato)}n-butylamine nickel (II) + 0.25% 2(2'-hydroxy-3',5'-di-t-butylphenyl)-5-chlorobenzotriazole | 75% | 47% | Brittle | | | |
| Blank * | 77% | 11% | Brittle | | | |

* Each of the samples tested and the control contains 0.2% of (di-n-octadecyl-3,5-di-t-butyl-4-hydroxybenzyl)phosphonate which is an antioxidant which prevents oxidative degradation of polypropylene.

EXAMPLE 11

High impact polystyrene resin containing elastomer (i.e., butadiene-styrene) is stabilized against loss of elongation properties due to exposure to ultraviolet light by incorporation of 0.3% by weight of N-methyl-N-n-octadecyl-β-alanine.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C and a pressure of 2,000 pounds per square inch (1.406 × 10$^6$ kilo per square meter) into a sheet of uniform thickness (25 ml) (0.0635 cm). The sheets are then cut into strips approximately 4 (10.16 cm) × 0.5 (1.27 cm) inches. A portion of these strips is then measured for percent of elongation in the Instron Tensile Testing Apparatus (Instron Engineering Corporation, Quincy, Massachusetts). The remaining portions of the strips are placed in an FS/BL chamber according to Example 9 (b) except that the samples are mounted and white cardboard stock and the time to 50% reduction in elongation is measured. The stabilized polystyrene resin retains its elongation property longer than the unstabilized resin.

EXAMPLE 12

Unstabilized linear polyethylene is solvent blended in methylene chloride with 0.5% by weight of the substrate of the nickel complex of N-methyl-N-n-octyl-β-alanine and then vacuum dried. The resin is then extrusion compounded on a 1 inch (2.54 cm) 24/1=L/D extruder, melt temperature 450° F (232° C) and pressed for 7 minutes at a temperature of 163° C and a pressure of 2000 psi (1.406 × $10^6$ kilo per square meter) into a sheet of uniform thicknesses of 100 mil. (0.254 cm). The sheets are then cut into plaques of 2 inch (5.08 cm) × 2 inch (5.08 cm). The plaques are then exposed in a FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 13

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (>1 mm) at 40°-45° C.

The dried rubber (25 g) is heated under nitrogen at 125° C in a Brabender mixer and to this is added with mixing 0.5% of the nickel complex of N-methyl-N-n-dodecyl-β-alanine. The composition is mixed for 5 minutes after which it is cooled and compression molded at 125° C into 5 inches (12.70 cm) × 0.025 inches plaques (0.0635 cm).

The plaques are exposed in a xenon arc weatherometer and the color measurement (L-b) is made after 45, 125 and 290 hours. The samples stabilized with the above compound are found to be much more light stable than the unstabilized samples.

EXAMPLE 14

To 50 g of polyacetal resin containing 0.1% of an acid scavenger, dicyandiamide, is added 0.2% by weight of the nickel complex of N-methyl-N-n-butyl-β-alanine and milled for 7 minutes at 200° C in a Brabender Plastirecorder. The milled formulation is subsequently pressed into a 40 mil (.102 cm) sheet at 215° C at 350 psi (2.461 × $10^5$ kilo per square meter) for 90 seconds then cooled quickly in a cold press at 350 psi (2.461 × $10^5$ kilo per square meter). The stabilized sheets are then remolded for 2 minutes at contact pressure and for 3 minutes at 300 psi (2.109 × $10^5$ kilo per square meter) at 215° C to give plaques 1½ inches (3.81 cm) × 2¼ inches (5.72 cm) × 125 mil (0.3175 cm). Thereafter, the light stability of the samples is tested through determination of surface crazing, chalking and/or color development after exposure in a carbon arc fadeometer. The stabilized samples are found to be much more than the unstabilized samples.

EXAMPLE 15

Unstabilized thoroughly dried polyethylene terephthalate chips are dry blended with 1.0% of the nickel complex of N,N-di-n-octyl-β-alanine. 60/10 denier multifilament is melt spun at a melt temperature of 290° C. The oriented fiber is wound on white cards and exposed in a Xenon Arc Fadeometer. Color measurements are made periodically with a Hunter Color Difference Meter Model D25. The stabilized samples are found to be much more light stable than the unstabilized samples.

EXAMPLE 16

(a) A composition comprising acrylonitrilebutadienestyrene terpolymer and 1% by weight of the nickel complex of N-methyl-N-p-n-dodecylphenyl-β-alanine resists embrittlement due to exposure to ultraviolet light longer than one which does not contain the stabilizer.

(b) A composition comprising polyurethane prepared from toluene diisocyanatc and alkylene polyols and 1.0% by weight of the nickel complex of α-methyl-N-methyl-N-n-octadecyl-β-alanine is more stable to sunlight, fluorescent sunlamps, black lights and fluorescent lights than the unformulated polyurethane.

(c) A composition comprising a polycarbonate prepared from bisphenol-A and phosgene and 1% by weight of the nickel complex of N-methyl-N-n-octadecyl-β-alanine resists discoloration due to exposure to ultraviolet light longer than one which does not contain the stabilizer.

(d) A composition comprising polymethylmethacrylate and 0.25% by weight of the nickel complex of N,N-diethyl-β-alanine resists discoloration due to exposure to ultraviolet light longer than one which does not contain the stabilizer.

EXAMPLE 17

(a) A stabilized polyamide (nylon 6,6) is prepared by incorporating therein 0.1% of the manganese complex of N-methyl-N-n-octadecyl-β-alanine. The light stability of the stabilized composition is superior to that of an unstabilized polyamide.

(b) A stabilized polyphenylene oxide polymer (prepared by polymerizing 2,6-dimethylphenol) is prepared by incorporating therein 0.5% by weight of the manganese complex of N-methyl-N-n-octadecyl-β-alanine. The stabilized compositions resist embrittlement due to exposure to ultraviolet light longer than one which does not contain the stabilizer.

(c) A stabilized crystalline polystyrene is prepared by incorporating therein 0.1% by weight of the zinc complex of N-methyl-N-n-octadecyl-β-alanine. The stabilized composition resists embrittlement due to exposure to ultraviolet light longer than one which does not contain the stabilizer.

Antioxidants may also be incorporated into each of the above mentioned compositions, for example, di-n-octadecyl-α,α'-bis(3-butyl-4-hydroxy-5-methylbenzyl) malonate 2,4-bis(4-hydroxy-3,5-di-t-butylphenoxy)-6-(n-octylthioethylthio)-1,3,5-triazine, 2,4-bis(3,5-di-t-butyl-hydroxyphenoxy)-6-(n-octylthio)-1,3,5-triazine di-n-octadecyl 3(3',5'-di-t-butyl-4-hydroxyphenyl)propionate, respectively.

What is claimed is:

1. A compound of the formula $$\left( \begin{matrix} R_1 \\ \phantom{R}\diagdown \\ \phantom{R}\phantom{N}N-\underset{\underset{\displaystyle }{|}}{\overset{\overset{\displaystyle R_3}{|}}{CH}}-\underset{\underset{\displaystyle }{|}}{\overset{\overset{\displaystyle R_4}{|}}{CH}}CO_2 \\ \phantom{R}\diagup \\ R_2 \end{matrix} \right)_n M \qquad I$$

wherein $R_1$ and $R_2$ independently of each other are alkyl, phenyl, phenyl substituted with 1 or 2 alkyl groups, cycloalkyl having 5 to 6 carbon atoms, benzyl or benzyl substituted with an alkyl group on the phenyl nucleus;

$R_3$ and $R_4$ are both independently hydrogen and lower alkyl;

M is a member selected from the group consisting of nickel, iron, chromium, manganese, zinc aluminum, tin, dialkyl tin and titanium; and $n$ has a value of from 1 to 4, the value of $n$ being the same as the available valence of M.

2. A compound according to Claim 1, wherein $R_1$ and $R_2$ independently of each other are alkyl having from 1 to 18 carbon atoms, cyclohexyl, phenyl, phenyl having an alkyl group to 1 to 12 carbon atoms at the 4-position of the phenyl ring, benzyl, or benzyl having an alkyl group of 1 to 12 carbon atoms at the 4-position of the phenyl ring;

$R_3$ and $R_4$ are independently hydrogen and lower alkyl; and

M is a member selected from the group consisting of nickel, chromium, manganese, zinc, aluminum, tin and dibutyltin.

3. A compound according to claim 2, wherein $R_1$ is alkyl having 1 to 18 carbon atoms, and $R_2$ is alkyl having 1 to 18 carbon atoms, phenyl, phenyl having an alkyl group of 1 to 12 carbon atoms at the 4-position of the phenyl ring, cyclohexyl, benzyl or benzyl having an alkyl group of 1 to 12 carbon atoms at the 4-position of the phenyl ring.

4. A compound according to claim 2, wherein $R_1$ and $R_2$ are independently of each other alkyl of from 1 to 18 carbon atoms, and M is a member selected from the group consisting of nickel, manganese, zinc and chromium.

5. A compound according to claim 2, wherein $R_1$ is methyl, $R_2$ is alkyl of from 4 to 18 carbon atoms, $R_3$ and $R_4$ are each hydrogen, and M is selected from nickel and manganese.

6. A compound according to claim 2 which is nickel bis(N-methyl-N-n-octyl-$\beta$-alanine).

7. A compound according to claim 2 which is nickel bis(N,N-di-n-octyl-$\beta$-alanine).

8. A compound according to claim 2 which is nickel bis(N-methyl-N-n-dodecyl-$\beta$-alanine).

9. A compound according to claim 2 which is nickel bis(N-methyl-N-n-octadecyl-$\beta$-alanine).

10. A compound according to claim 2 which is manganese bis(N-methyl-N-n-octadecyl-$\beta$-alanine).

11. A compound according to claim 2 which is nickel bis(N-methyl-N-n-butyl-$\beta$-alanine).

12. A compound according to claim 2 which is nickel bis(N-methyl-$\alpha$-methyl-N-n-octadecyl-$\beta$-alanine).

13. A compound according to claim 2 which is nickel bis(N-methyl-$\beta$-methyl-N-n-octadecyl-$\beta$-alanine).

14. A compound according to claim 2 which is nickel bis(N,N-di-n-propyl-$\beta$-alanine).

15. A compound according to claim 2 which is nickel bis(N,N-diethyl-$\beta$-alanine).

16. A compound according to claim 2 which is nickel bis(N-methyl-p-n-dodecylphenyl-$\beta$-alanine).

17. A composition of matter stabilized against ultraviolet deterioration which comprises a synthetic organic polymer normally subject to ultraviolet deterioration containing from (a) 0.005% to 5% of a stabilizing compound according to claim 1, (b) 0 to 5% of a phenolic antioxidant, (c) 0 to 5% of a thio co-stabilizer, and (d) 0 to 5% of a UV absorber.

18. A composition of claim 17 wherein the organic material is a polyolefin.

19. A composition of claim 18 wherein the polyolefin is polypropylene.

* * * * *